US012575946B2

(12) United States Patent
Frey et al.

(10) Patent No.: US 12,575,946 B2
(45) Date of Patent: Mar. 17, 2026

(54) PATIENT-MATCHED MODULAR IMPLANTS AND INSTRUMENTS

(71) Applicant: Mighty Oak Medical, Inc., Englewood, CO (US)

(72) Inventors: George Frey, Englewood, CO (US); Caleb Voelkel, West Grover, VT (US); Austin Clemens, Denver, CO (US); Tyler Drumm, Littleton, CO (US)

(73) Assignee: Mighty Oak Medical, Inc., Englewood, CO (US)

( * ) Notice: Subject to any disclaimer, the term of this patent is extended or adjusted under 35 U.S.C. 154(b) by 193 days.

(21) Appl. No.: 18/377,162

(22) Filed: Oct. 5, 2023

(65) Prior Publication Data

US 2024/0115398 A1      Apr. 11, 2024

Related U.S. Application Data

(60) Provisional application No. 63/413,427, filed on Oct. 5, 2022.

(51) Int. Cl.
    *A61F 2/44*       (2006.01)
    *A61F 2/46*       (2006.01)
    *A61F 2/30*       (2006.01)
(52) U.S. Cl.
    CPC .......... *A61F 2/4611* (2013.01); *A61F 2/4455* (2013.01); *A61F 2002/30329* (2013.01)
(58) Field of Classification Search
    CPC ...... A61F 2/442; A61F 2/4425; A61F 2/4455; A61F 2002/443

USPC ............................................. 623/17.11–17.16
See application file for complete search history.

(56) References Cited

U.S. PATENT DOCUMENTS

| | | | |
|---|---|---|---|
| 6,159,211 A | * 12/2000 | Boriani | ................. A61F 2/4455 606/279 |
| 8,465,547 B2 | 6/2013 | Melkent et al. | |
| 8,540,770 B2 | 9/2013 | Woodburn | |
| 8,992,616 B2 | * 3/2015 | Chappuis | .............. A61F 2/4455 623/17.11 |
| 9,526,627 B2 | 12/2016 | Tabor et al. | |
| 9,636,233 B2 | 5/2017 | Arnold | |
| 10,675,158 B2 | 6/2020 | Unger | |
| 11,304,824 B2 | 4/2022 | Ali | |
| 11,723,779 B2 | * 8/2023 | Ryan | ........................ A61F 2/447 623/17.16 |
| 2015/0305878 A1 | 10/2015 | O'Neil | |
| 2018/0280142 A1 | * 10/2018 | Schultz | .............. A61F 2/30749 |
| 2021/0106437 A1 | 4/2021 | de Villiers et al. | |
| 2022/0031469 A1 | * 2/2022 | Suh | ......................... A61F 2/447 |

* cited by examiner

*Primary Examiner* — Eduardo C Robert
*Assistant Examiner* — Christina Negrellirodriguez
(74) *Attorney, Agent, or Firm* — FisherBroyles LLP; Ian R. Walsworth

(57)                    ABSTRACT

The following relates to patient-specific or patient-matched, customized apparatus for use in surgical procedures, including various interbody procedures. The patient-matched apparatus may be a modular implant, a monolithic implant, and may include an instrument for use in procedures involving a modular or monolithic implant. One or more patient-matched apparatus described herein may be configured for use with a guide, with robotic instrumentation, or with augmented reality system.

19 Claims, 10 Drawing Sheets

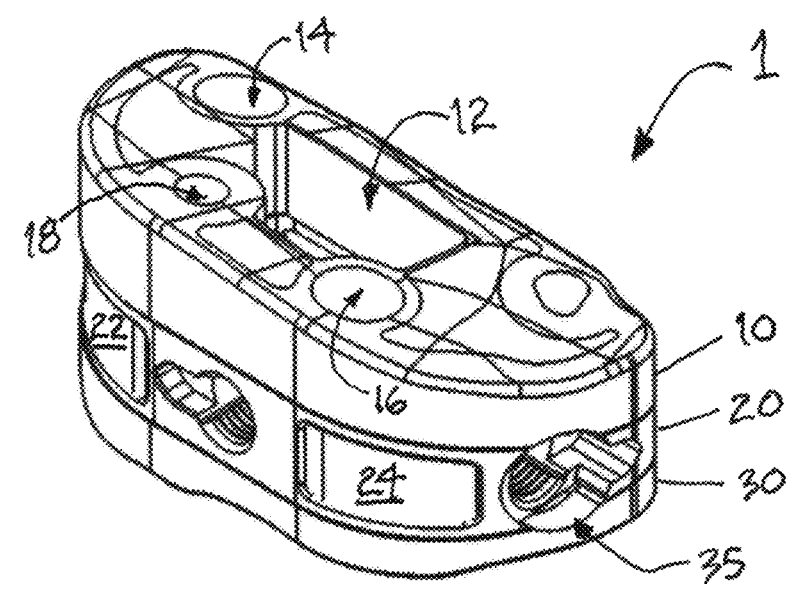
FIG. 1A
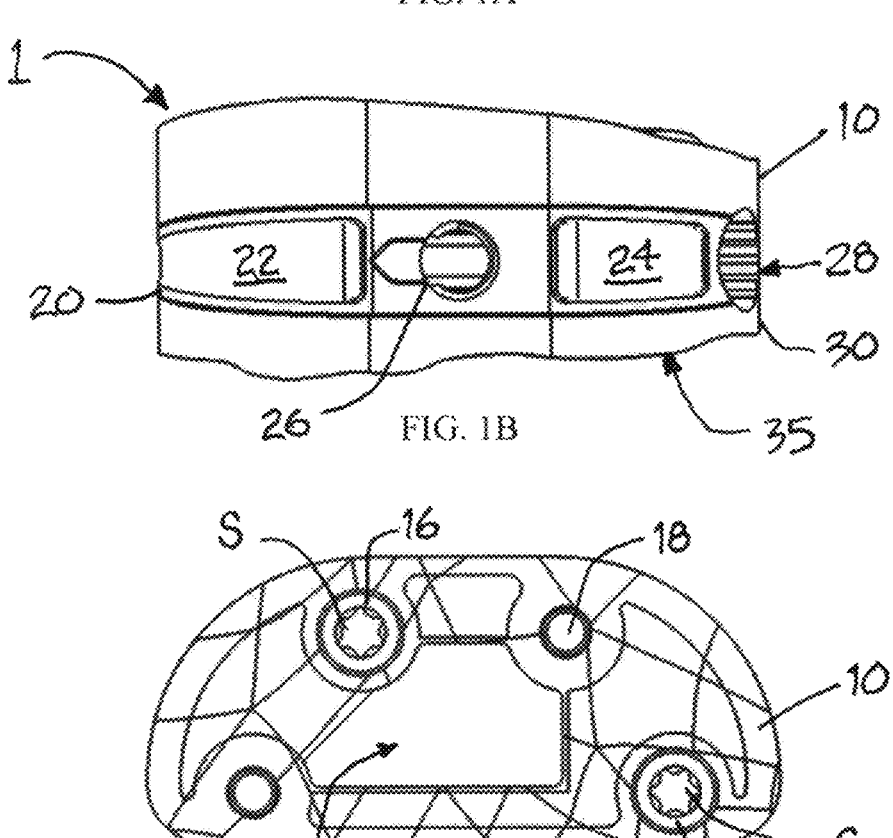
FIG. 1B
FIG. 1C

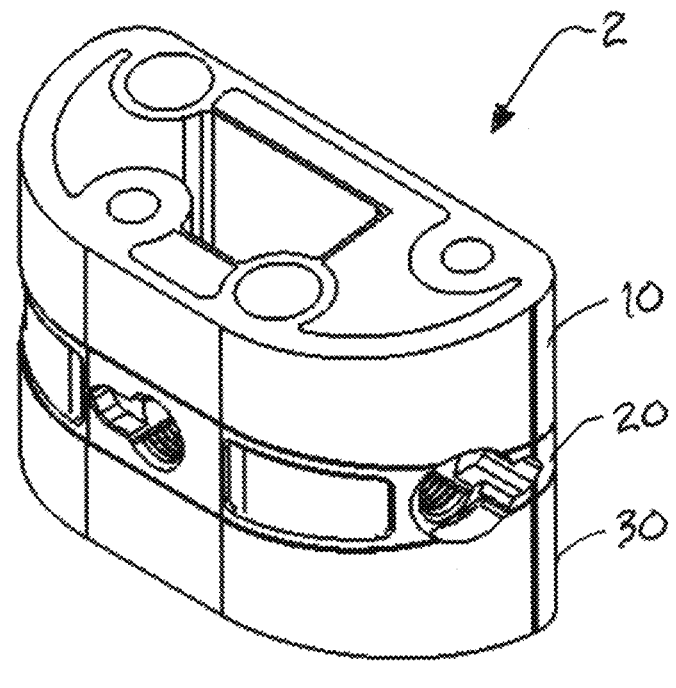
FIG. 7A
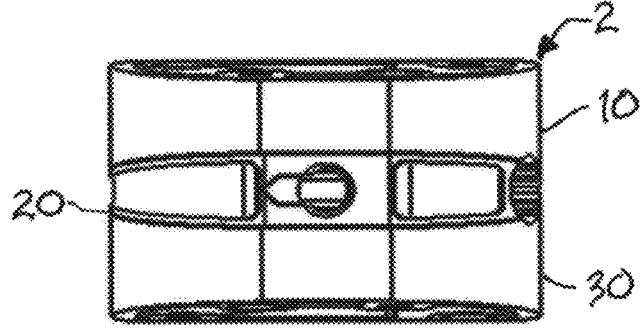
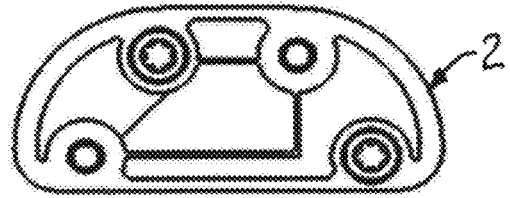
FIGS. 7B-C

FIGS. 8B-C

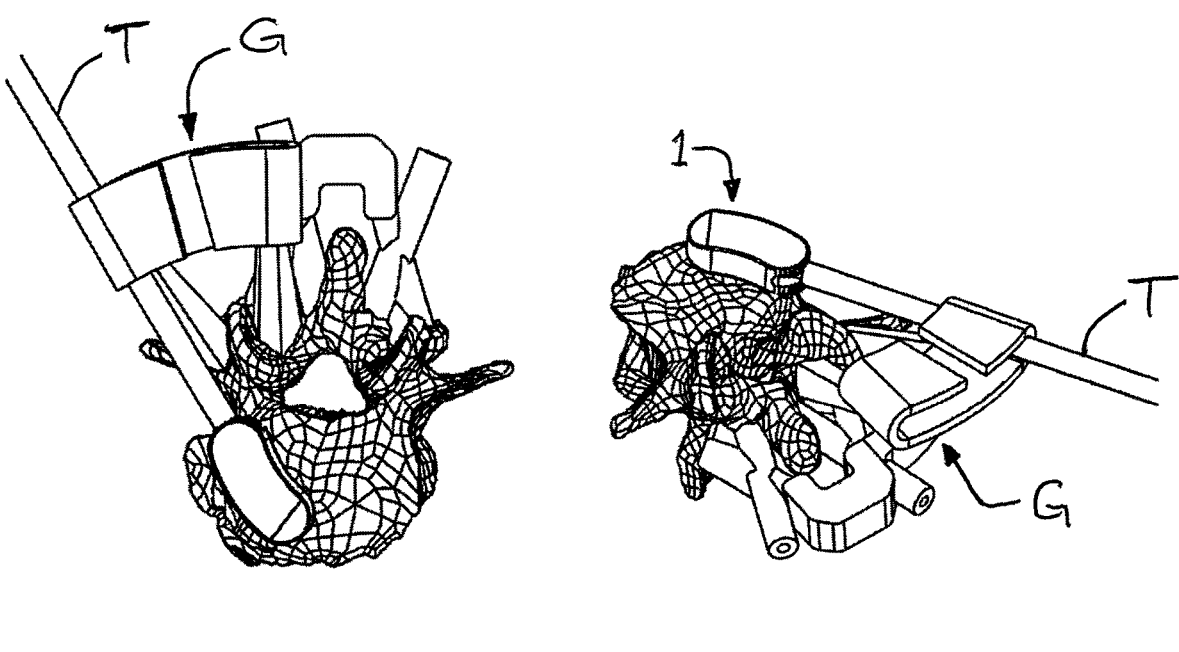
FIG. 11A                    FIG. 11B
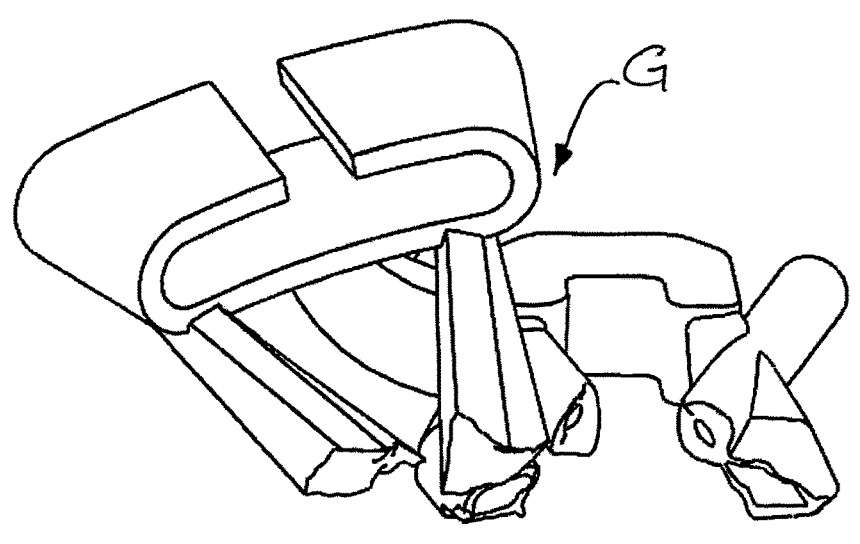
FIG. 12

PATIENT-MATCHED MODULAR IMPLANTS AND INSTRUMENTS

CROSS REFERENCE TO RELATED APPLICATIONS

This application claims priority, pursuant to 35 U.S.C. § 119(e), to U.S. Provisional Patent Application No. 63/413,427, filed on Oct. 5, 2022, which is incorporated by reference herein in its entirety.

FIELD OF THE INVENTION

The present disclosure generally relates to the field of medical devices, and more specifically toward patient-specific or patient-matched surgical devices, including intervertebral implants and instruments, based on the patient's unique anatomical features. The present disclosure also relates to methods of manufacturing and using the same.

BACKGROUND OF THE INVENTION

Given the complexities of surgical procedures and the various tools, instruments, implants and other devices used in the procedures, as well as the varying anatomical differentiation between patients who receive those tools, instruments, implants and devices, it is often challenging to create a surgery plan to accounts for the unique and sometimes irregular anatomical features of a particular patient. For example, the implantation of orthopedic screws or other fixation devices in a patient's boney anatomy is well accepted amongst surgeons who treat various orthopedic pathologies. Although the performance of various screw constructs has become predictable, there are still multiple challenges with the placement and insertion of the orthopedic screws or other fixation devices. The challenges occur, for example, when a surgeon is unable to reference boney landmarks due to previous surgery or when the patient's anatomy is irregular in shape, or when a particular trajectory for insertion of the screws (or other fixation devices) is impeded by anatomical obstructions.

Surgeons now have the ability to readily convert magnetic resonance imaging (MRI) data or computed tomography (CT) data into a data set readable by computer-aided design (CAD) program and/or finite element modeling (FEM) program, which then may be used to create, for example, a customized surgical guide and/or implant based on the dynamic nature of the anatomical structures the customized guide/implant is designed to associate with. This data, while currently used by surgeons in surgery planning, is largely unused for creating a customized set of instruments or other surgical devices that are designed to complement the patient's unique anatomy.

Spinal discs degenerate over time as anatomical loading, trauma and other external factors stress these particular segments of the spine. When degeneration occurs to a certain degree, neurologic and musculoskeletal issues may arise unless the disc segment is restored to its natural anatomical height. Fusion (i.e. a solid column of bone) from the upper to the lower vertebral endplates is the goal of a lumbar intervertebral fusion surgery such that the restored disc height is permanent and mobility is inhibited in this particular segment. Intervertebral fusion devices are used to restore the disc's natural anatomical height. These devices also facilitate transfer of bone graft or enhanced biologics to stimulate bone growth.

Other pathologies that may be treated are idiopathic scoliosis, degenerative scoliosis and spondylolisthesis. These conditions define a patient possessing vertebral end-plates and anatomical landmarks in abnormal positions and angular relationships. Intervertebral fusion procedures may be used to help correct positional and angular imbalance and effectively realign abnormal anatomy. Depending on surgeon and patient pathology, different surgical approaches may be used such as Posterior Lumbar Interbody Fusion (PLIF), Transforaminal Lumbar Interbody Fusion (TLIF), Anterior Lumbar Interbody Fusion (ALIF), Oblique Lumbar Interbody Fusion (OLIF), Transforaminal Lumbar Interbody Fusion Oblique (TLIFO) and Extreme Lateral Interbody Fusion (XLIF). The patient-matched apparatus disclosed in this application is not limited to any one of these approaches.

Virtual reality and/or augmented reality systems (collectively referred to as "AR" in this disclosure) have provided advantages to surgeons with respect to surgical planning and in particular the ability of surgeons to visual the orientation and placement of orthopedic implants and/or instruments. The surgeon would therefore benefit from the enhanced ability to merge AR capabilities with patient-specific surgical devices and/or equipment, as well as customized manufacturing and placement of patient-specific guides/implants. While various types of augmented reality (AR) systems are provided in the prior art, several are not applicable or usable with the current state of surgical equipment, including those AR systems that pertain to driving assistance for vehicles, games, and entertainment attractions. In addition, different localization methods may be used with prior art AR systems, such as sensor-based localization methods relying on the use of many sensors. As another example, certain AR systems rely on a global positioning system (GPS) sensor and/or an inertial measurement unit (IMU) sensor to verify a location and a direction of an object. When high accuracy is required, a sensor-based localization method requires a specific (and often expensive) sensor with a high degree of accuracy, but is not practical in surgical settings. Furthermore, many prior art vision-based localization methods rely on specific camera information to acquire highly precise information, yet are difficult to use in a surgical environment.

Specific surgical procedures may also be performed in the spinal and/or cephalad region of a patient. The procedures performed in these areas are often designed to stop and/or eliminate all motion, including by removal and/or destruction of some or all of the boney anatomy in the patient's boney anatomy and/or implantable fixation devices (i.e., plates or screws) for limiting movement of the boney anatomy of the particular patient. By eliminating movement, pain and degenerative disease may be reduced or avoided.

A significant danger of performing operations on a patient's orthopedic anatomy, and in particular accessing an intervertebral space during a MIS surgery on the spine, is that of inadvertently contacting or damaging the para-spinal nerves, including the exiting nerve roots, traversing nerves and the nerves of the cauda equina. The exact location of these para-spinal nerves cannot be precisely determined prior to the commencement of surgery, and therefore are dependent on a surgeon's ability to visually locate the same after the initial incision is made. Moreover, intervertebral spaces in the spine have other sensitive nerves disposed at locations which are not entirely predictable prior to insertion of the surgical tool into the intervertebral area. Accordingly, the danger of pinching or damaging spinal nerves when accessing an intervertebral space has proven to be quite limiting to the methods and devices used during minimally invasive spinal surgery. In addition, as cannula are received through the patient's back, such as when performing minimally invasive spinal surgery, minor blood vessels are ruptured, thereby blocking the surgeon's vision inside the intervertebral region after the cannula has been inserted. Other anatomical features at a particular patient may also obstruct the surgeon's view or make it difficult to provide illumination within the cannula. Therefore, one particular shortcoming that is addressed by the present disclosure is to provide devices which are patient-matched to facilitate proper location and orientation without use of microscopes or other equipment and that otherwise eliminate the problems associated with prior art procedures on the spine, including MIS procedures.

As described herein, the prior art fails to teach a system for creating patient-specific or patient-matched surgical apparatus, based on the data set derived from the MRI or CT scan, for use with robotic and AR systems. The use of the patient-specific data set for a vertebral or other anatomic body of a particular patient may allow a surgeon to accommodate for subtle variations in the position and orientation of a screw, plate or other bone anchor to avoid particular boney anatomy or irregularities in the positioning and alignment of the adjoining vertebral bodies.

As another example, the use of these data sets may also assist a surgeon in selecting a desired trajectory for an implantable device so as to avoid sensitive anatomical features of a particular patient or to secure a bone anchoring device in a particular area of desired bone density during an actual procedure. The use of patient-specific data sets further permits the surgeon to avoid mistakes by creating customized tools and instruments, which may comprise orientation, end-stops or other safety related features to avoid over-torque and/or over-insertion of any implantable devices. The use of patient-specific data sets also permit the surgeon to create a patient-contacting surface that is oriented to match one or more of the anatomical features represented by the data set, and thereby quickly and efficiently locate and place the patient-contacting surface(s) in the appropriate location and orientation.

It would therefore be advantageous to provide implants, instruments and other apparatus suitable for use with a surgical procedure on a specific patient. It would also be advantageous to provide a customized surgical plan based on the patient's unique characteristics and/or one or more medical devices that are adapted to conform to a plurality of anatomical features of a particular patient. It would also be advantageous to provide apparatus and methods to assist a surgeon in completing the surgical procedure(s) safely and efficiently. Finally, it is also advantageous to provide a procedure and/or apparatus that otherwise significantly reduces, if not eliminates, the problems and risks noted above. Other advantages over the prior art will become known upon review of the Summary and Detailed Description of the Invention and the appended claims.

SUMMARY OF THE INVENTION

By way of providing additional background, context, and to further satisfy the written description requirements of 35 U.S.C. § 112, the following patent applications and patents are incorporated by reference in their entireties for the express purpose of explaining and further describing patient-matched and/or patient-specific spinal implants and other apparatus associated with surgical procedures, including minimally invasive surgery procedures: U.S. patent application Ser. No. 16/831,215, filed on Mar. 26, 2020; U.S. patent application Ser. No. 16/598,861, filed on Oct. 10, 2019; U.S. patent application Ser. No. 15/997,404, filed Jun. 4, 2018; U.S. Pat. No. 9,987,024, which issued on Jun. 5, 2018; U.S. Pat. No. 9,642,633, which issued on May 9, 2017; U.S. Pat. No. 9,198,678, which issued on Dec. 1, 2015; U.S. Pat. No. 8,870,889, which issued on Oct. 28, 2014; and U.S. Pat. No. 8,758,357, which issued on Jun. 24, 2014.

The present disclosure relates to patient-specific or patient-matched surgical devices, including intervertebral implants and TLIF instruments. As one of ordinary skill in the art will understand, orthopedic and other surgeries may be performed by a number of different procedures, as opposed to conventional surgical procedures and methods, which typically require cutting of muscles, removal of bone, and retraction of other natural elements. During a mini-mally-invasive surgical (MIS) procedure, for example, including procedures using the apparatus of the present invention, a less destructive approach to the patient anatomy is carried out by using retractor tubes or portals, which take advantage of anatomy and current technology to limit the damage to intervening structures. Thus, it is to be expressly understood that various surgical procedures using the apparatus and systems described herein may be performed, including with sequential or simultaneous introduction of rods, pins, plates, screws or other surgical devices into adjacent boney anatomy, to achieve a fusion or otherwise join various portions of the vertebrae of a particular patient.

Current implants and vertebral replacement systems are offered in a variety of sizes, but are offered in standard configurations. For example, a certain interbody implant may be offered in two footprints: 40 mm L×18 mm W; and 50 mm L×22 mm W. That same implant may be offered in a variety of heights: 8, 10, 12 mm, etc. The implant may also be offered with a variety of wedge angles: 8, 14°, 20°, etc. Based on "measuring" an intervertebral space, a surgeon is able to determine the approximate size device needed, then chooses said device configuration for implantation. As factors may change during the surgical operation (access site is difficult to reach, anatomical forces do not allow for the proper implant fit, the surgeon over prepares the disc space and removes more bone than anticipated), the ability to intraoperatively adjust the surgical plan has become increasingly important to the success of a surgical procedure.

Surgeons and medical professionals now have the ability to pre-surgically plan the optimal size of the interbody device (L, W, H, and Angle), such that the surgeon understands the optimal size to be implanted prior to surgery and the range of choices required to satisfy the surgical operation are reduced. Therefore, in one aspect of the present disclosure, the use of a modular, patient-matched implant eliminates the need to carry 20 or more configurations of an implant for accommodating different patients' needs. Instead, the surgeon may be provided with two patient specific endplates (one upper and one lower), along with a common component. The entire implant assembly may be quickly assembled via two or more assembly screws.

As such, the invention provides the surgeon with the benefit of a patient-matched or patient-specific component by offering morphologically matched device endplates to the patient's vertebral endplates, while providing the ability to adjust device sizing intraoperatively by adjusting the common component. This essentially provides the surgeon with the best of the current standard solution (a large variety of sizes, shapes, etc.) and the benefits of a patient specific device (morphologically matched device endplates).

Accordingly, one aspect of the present disclosure is to provide a patient-matched modular or monolithic implant such as the one depicted in the drawing Figures appended hereto.

In another aspect, a patient-matched device for use in a TLIF, ALIF or DLIF procedure is disclosed. The device may be coupled with an instrument and/or a patient-matched surgical guide to facilitate connection, insertion and placement of the device to the location in which it was planned. Reference is again made to FIGS. 1-12 for additional details and illustrations of this device.

In another aspect, one or more patient-matched instruments are provided that connect directly with the patient-matched implant. While the instrument having a direct connection may provide for an uninterrupted interface for impaction, the instrument may alternatively be coupled with the patient-matched surgical guide to provide enhanced angular and positional constraints, such that the implant may be delivered to its intended location.

According to yet another embodiment, data obtained from the patient permits the apparatus to be manufactured with defined openings and/or apertures in the body of the implant, which are operatively associated with at least one instrument, and which permit the at least one instrument to be inserted in a consistent and reproducible manner. Examples implantable devices include but are not limited to spacers, replacement joints, replacement systems, cages, etc. The surgical guide may comprise one or more stops for preventing an instrument or implant from advancing beyond a predetermined distance.

According to one aspect, the invention relates to a modular, patient-matched implant assembly, comprising: an upper endplate; a lower endplate; a medial component selectively positionable between the upper endplate and the lower endplate and comprising at least a top surface and a bottom surface; the upper endplate comprising a first surface and a second surface, the first surface comprising one or more patient-specific contours determined from the anatomical data of a specific patient, the second surface complementary to the top surface of the medial component; the lower endplate comprising a first surface and a second surface, the first surface comprising one or more patient-specific contours determined from the anatomical data of a specific patient, the second surface complementary to the bottom surface of the medial component; the upper endplate, lower endplate and medial component configurable to be joined together by one or more screws.

According to another aspect, a method is disclosed comprising the following steps: acquiring patient anatomical data, preferably in the form of images (such as a CT scan); segmenting and converting the data into a 3D model representative of the patient anatomical data; adjusting the 3D model based upon input from at least one individual; determining the maximum length, width, height and wedge angle(s) for the specific patient; determining the maximum footprint of a device that is able to conform to the patient anatomical data; determining the height and wedge angle of a device for manufacture specific to the patient; determining the desired dimensions of the medial component of the device; determining the dimensions of the upper and lower endplates, including: (a) defining contours of an upper surface of the upper endplate to match the lower surface of the adjacent vertebral body; (b) defining contours of a lower surface of the upper endplate to match the upper surface of the medial component; (c) defining the contours of a lower surface of the lower endplate to match the upper surface of the adjacent vertebral body; and (d) defining the contours of an upper surface of the lower endplate to match the lower surface of the medial component.

In embodiments, patient-matched devices may comprise a surgical guide that is oriented in at least one trajectory. The surgical guide may be used with one or more patient-matched instruments for achieving, by way of example, a transforaminal lumbar interbody fusion (TLIF), a posterior lumbar interbody fusion (PLIF), a direct lumbar interbody fusion (DLIF), an anterior lumbar interbody fusion (ALIF), an oblique lumbar interbody fusion (OLIF), a transforaminal lumbar interbody fusion oblique (TLIFO), an extreme lumbar interbody fusion (XLIF), or a cervical interbody trajectory or approach to the patient's vertebrae. In other embodiments, the trajectory may be one of: a cervical pedicle screw trajectory; a pedicle screw trajectory; a cortical or cortical bone trajectory; a sacral pedicle trajectory; a sacral alar trajectory; an S2-alar-iliac trajectory; an iliac trajectory; a transarticular trajectory; a lateral mass trajectory; a translaminar trajectory; a transcondylar trajectory; and an occipital trajectory (for example, during an operation on a patient's occipital or surrounding cervical anatomy).

In embodiments, patient-specific or patient-matched devices described herein may be used with various orientation or registration markers for identification by a robot. Certain devices may comprise an embedded chip, circuit or equivalent with presurgical planning information, which may be read by a machine and deliver specific instructions to a robotic surgical device, for example. Such patient-specific apparatus may be used on multiple levels of a patient's spine that are impacted by a particular surgical procedure, and thereby provide markers for registration and orientation without having to rescan the patient throughout the surgery. The robotic device may view the patient and position of the patient's unique anatomy through the identification of the markers, and thereby more rapidly align instrumentation controlled by the robotic equipment.

In embodiments, the patient-matched devices described herein may comprise a locating feature for a robot or other autonomous device to align the guide to a vertebra in space, for example. With multiple devices placed on a patient's vertebra, a robot can validate location of the underlying anatomy, drill into the vertebra, affix an orientation tool, and/or orient vertebra relative to each other to meet presurgically planned spinal alignment. Pre-surgically planned spinal alignment may also be matched to one or more pre-bent rods, minimizing surgical time. In other embodiments, the robot or other autonomous device may be configured to perform one or more cuts (i.e., osteotomy) with known locations of vertebra relative to each other.

In embodiments, the surgical devices described herein may be used with an AR system or associated simulation device. In one embodiment, the AR capabilities are provided in conjunction with a physical device, while in other embodiments the capabilities are provided in conjunction with a "virtual" device. In one embodiment, the surgical device is configured as a patient-specific guide for use with a surgical instrument or implantable device. The guide is preferably adapted to guide intra-operative placement of implants and/or screws that are used to anchor an implant and/or screw onto target portion of a patient's anatomy. In one embodiment, the target portion of the patient's anatomy is a posterior element of the patient's spine, including lumbar, interbody and cervical portions of a patient's spine.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the claims set forth herein below define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures. It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein. In the drawings:

FIG. 1A is a perspective view of a patient-matched, modular implant assembly according to embodiments of the present disclosure;

FIG. 1B is a front elevation view of the implant assembly shown in FIG. 1A;

FIG. 1C is a top plan view of the implant assembly shown in FIG. 1A;

FIGS. 7A-C are various views of a patient-matched, modular implant according to another embodiment of the present disclosure;

FIGS. 8A-C are various views of another patient-matched, modular implant according to one embodiment of the present disclosure;

FIGS. 11A-B are perspective views of a guide and instrument for use with the patient-matched, modular implant according to embodiments of the present disclosure;

FIG. 12 is another perspective view of the guide shown in FIGS. 11A-B;

DETAILED DESCRIPTION

Figures 2A, 2B, 2C:
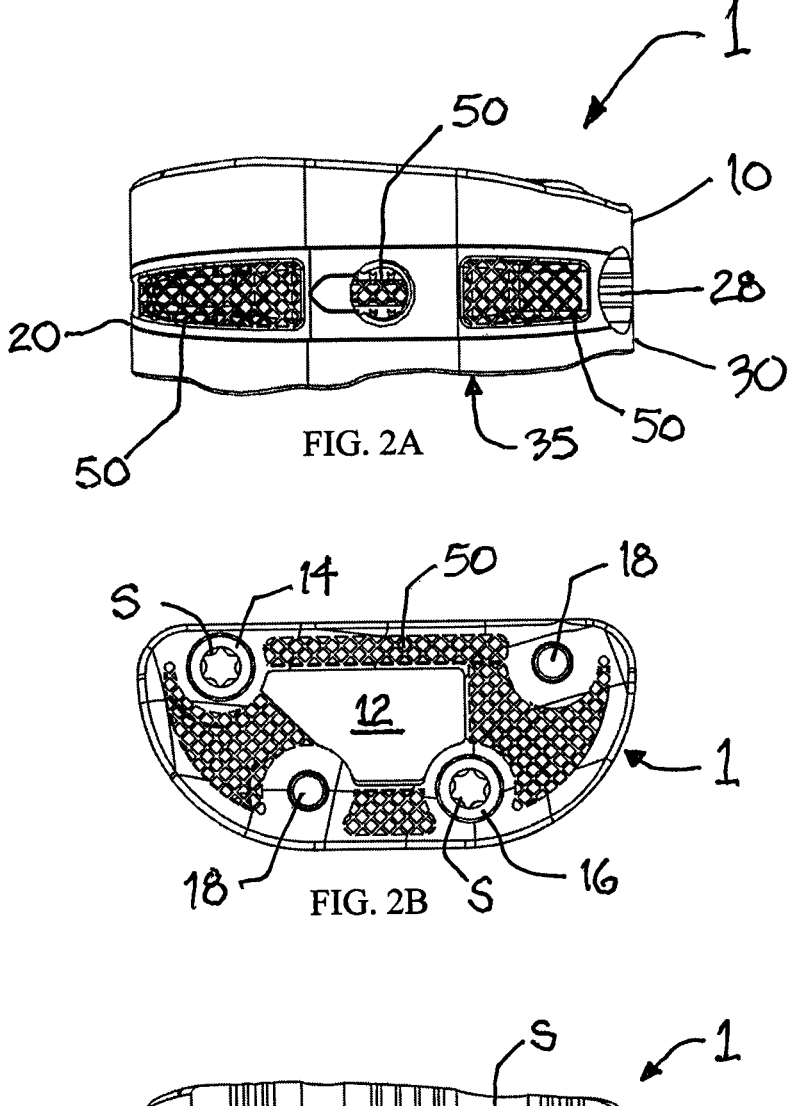
FIG. 2A is a front elevation view of a patient-matched, modular implant assembly according to another embodiment of the present disclosure.
FIG. 2B is a top plan view of the implant assembly shown in FIG. 2A.
FIG. 2C is a partial sectional view of the implant assembly shown in FIG. 2A.

As shown in FIGS. 1-14 and described in further detail herein, the present disclosure relates to a novel system and method for design and use of a customized, patient-matched apparatus in a diverse number of surgical procedures, including TLIF, ALIF, DLIF, PLIF, OLIF, XLIF, TLIFO and cervical interbody surgeries. The customized, patient-matched apparatus in one embodiment is provided as a modular, patient-specific interbody implant. The patient-matched implant may be assembled by a surgeon or other medical professional prior to surgery or, in certain embodiments, in situ. The implant may be comprised of one or more patient-matched components and one or more standard components. The one or more standard components may be provided in different sizes or dimensions, thereby permitting a surgeon to select and configure the patient-matched implant according to a desired height. In certain embodiments, the implant may be self-distracting.

In embodiments, the patient-matched apparatus described herein may be configured for use with: a TLIF trajectory; an ALIF trajectory; a DLIF trajectory; a PLIF trajectory; a TLIFO trajectory; an OLIF trajectory; a XLIF trajectory; a cervical interbody trajectory; a cervical pedicle screw trajectory; a pedicle screw trajectory; a cortical or cortical bone trajectory; a sacral pedicle trajectory; a sacral alar trajectory; an S2-alar-iliac trajectory; an iliac trajectory; a transarticular trajectory; a lateral mass trajectory; a translaminar trajectory; a transcondylar trajectory; or an occipital trajectory.

According to preferred embodiments, the patient-matched apparatus preferably uses a patient's unique morphology, which may be derived from capturing MRI data, CT data, or any other medical imaging device to derive one or more patient-matched surfaces, elements or components, which comprise complementary surfaces to those encountered during the surgical procedure(s) as derived from a set of data points. The apparatus may further comprise unique indicia, markers or equivalent for registration with the types of autonomous or augmented equipment described above.

According to various embodiments described herein, the patient-matched apparatus may be used with a specific instrument or tool, and may further comprise desired axes and/or insertional trajectories. According to embodiments, one patient-matched apparatus described herein may be further matched with at least other apparatus described herein for use during a particular surgical procedure. By way of example but not limitation, a patient-matched modular implant may be matched with a TLIF instrument for inserting and positioning the patient-matched implant between two vertebrae.

The apparatus may be configured to receive markers or may include markers embedded within the apparatus, the position of which (relative to the patient-contacting and other elements/components of the apparatus) are easily registered and determined by the autonomous or augmented equipment employed during the procedure. Other features of the disclosure will become apparent after a review of the following disclosures and varying embodiments of the disclosure.

Embodiments of a patient-matched or patient-specific apparatus according to certain aspects are depicted in FIGS. 1-14. In embodiments, the apparatus is a novel type of intervertebral implant referred to herein as a modular implant, and is adapted to fit directly to aspects of a patient's anatomy. The term "modular" is used herein in a non-limiting sense and is for convenience only. According to another embodiment, the patient-matched apparatus is a monolithic implant. According to yet another embodiment, the patient-matched apparatus is a vertebral body replacement system. In specific embodiments described herein, the implant is specifically configured for a TLIF, ALIF or DLIF procedure.

Referring now to FIGS. 1A-C, multiple views of a patient-matched, modular implant assembly 1 are depicted. The patient-matched implant assembly 1 may be comprised of an upper endplate 10, lower endplate 30, medial component 20 which constitute the assembly. The upper endplate 10 and lower endplate 30 are designed to be patient-matched or patient specific. The medial component 20 is designed to be a more standard component and available in a plurality of configurations where the length, width, height and angle are pre-set or pre-determined.

The implant assembly may comprise apertures 22-24, which decrease the volume and/or weight of the assembly while providing areas for inserting bone graft, allograft, autograft or other growth promoting biologic material. Ther assembly may further comprise a central aperture 12 for this same purpose. The assembly may comprise one or more bores 14, 16, 18 for receiving assembly screws S (shown in FIG. 1C) or alternatively pins (shown in FIG. 14A), which facilitate assembly of the upper endplate 10, lower endplate 30 and medial component 20. Bores 14, 16, 18 may be substantially cylindrical and may comprise threading for securely receiving a threaded screw S. In certain embodiments, the threading may be present only along a portion of bores 14, 16, 18. Instrument attachment joints 26, 28 may also be provided, and may include a keyed interface to facilitate alignment of an instrument or tool as described in detail below.

Patient contacting portions 35 of the modular implant 1 are designed based on the patient's anatomical data. In embodiments, these portions are preferably additively manufactured. In this manner, the upper and lower endplates 10, 30 are customized for a particular patient such that the patient-contacting surfaces are complementary to, and conform closely to, the geometries of the adjacent vertebral bodies. In preferred embodiments, the medial component 20 is manufactured using traditional methods known to those of ordinary skill in the art, however, in alternate embodiments the medial component 20 is additively manufactured. In yet further embodiments, the medial component 20 is generic and/or not patient-specific, which allows the user to carry fewer components and use standardized medial bodies 20 with various patients and/or surgical procedures.

FIGS. 2A-C show multiple views of a patient-matched, modular implant assembly 1 according to another embodiment. In certain configurations, the implant 1 may comprise one or more porous structures 50. In embodiments, these porous structures may facilitate fusion by providing a lattice-like structure, wherein bone growth occurs between the modular implant assembly 1 and the surrounding boney anatomy. The use of porous structures 50 is also advantageous in providing and promoting bone growth throughout the modular implant 1, and more closely resembles the biomechanical properties of human boney anatomy. The porous structures 50 may be substantially throughout the interior of the implant assembly 1 as shown in FIG. 2B, or may be in fewer, specified locations on the upper endplate 10, lower endplate 30, or medial component 20.

A sectional view of the implant assembly 1 is shown in FIG. 2C, wherein the screws S are shown in relation to the assembled upper endplate 10, lower endplate 30 and medial component 20. As can be seen in FIG. 2C, the distal ends of the implant assembly 1 include openings in communication with a central chamber 40.

Figure 3:
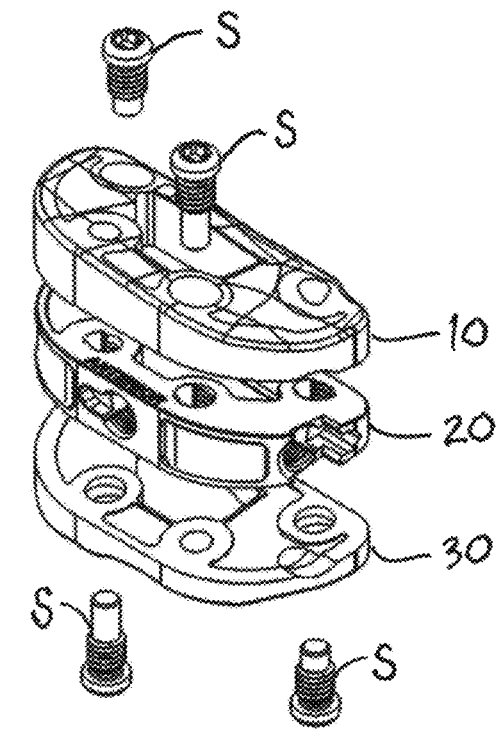
FIG. 3 is an exploded view of the implant assembly shown in FIG. 1A.
Figure 4:
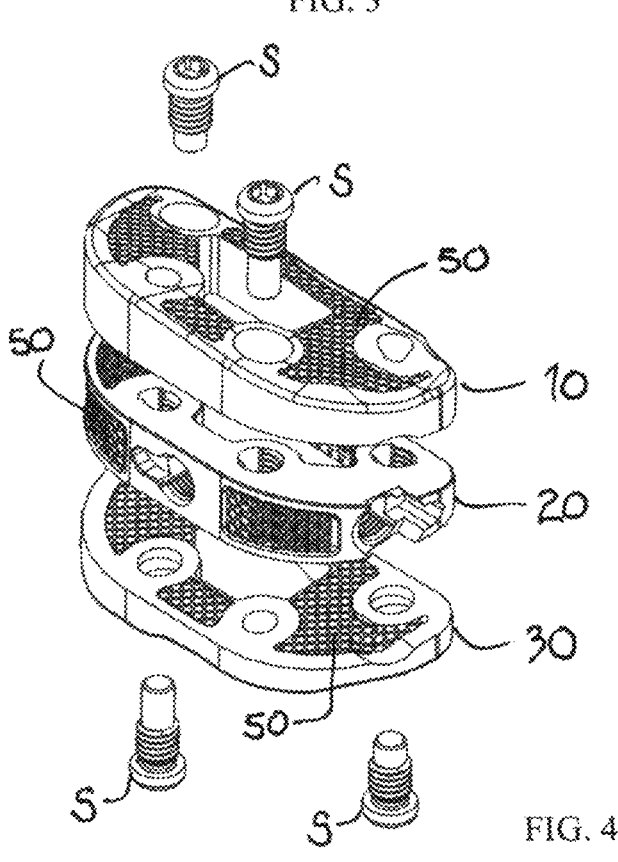
FIG. 4 is an exploded view of the implant assembly shown in FIG. 2A.

FIGS. 3-4 depict exploded views of the patient-matched, modular implants shown in FIGS. 1A and 2A. These embodiments may comprise porous structures 50 as shown in FIG. 4. Alternatively, the implant assembly 1 may be substantially solid about the patient-contacting surfaces as shown in FIG. 3. Porous regions of the medial component 20 and/or endplates 10, 30 may be standard and pre-defined. Porous regions of the medial component 20 and endplates 10, 30 may be patient-specific and determined through patient imaging techniques known to those of ordinary skill in the art (CT, DEXA, etc.). Porous regions may possess a gradient in pore sizes that are patient specific and determined through patient imaging. In certain embodiments, screws S may be inserted through the upper endplate 10 and lower endplate 30, while in other embodiments only a single screw S may be necessary. In other embodiments, one or more pins may be used in lieu of or in addition to screws S.

Figure 5:
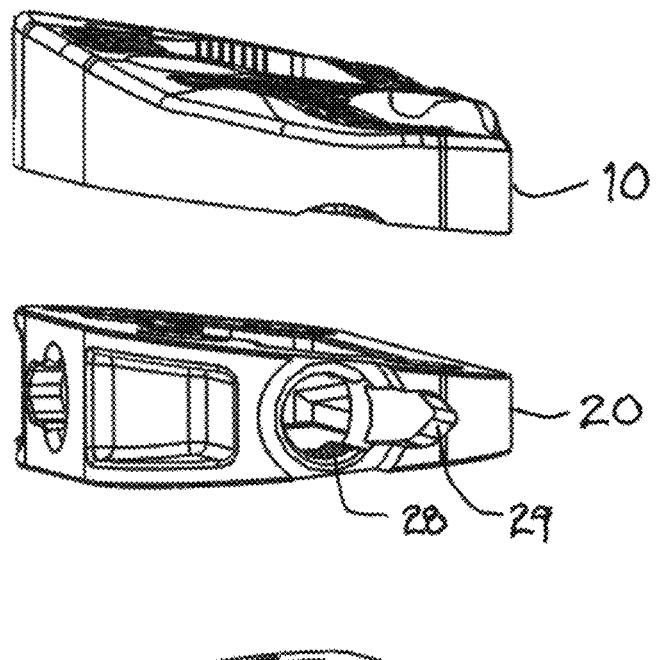
FIG. 5 shows multiple perspective views of a patient-matched, modular implant assembly according to another embodiment of the present disclosure.

FIG. 5 shows multiple perspective views of a patient-matched, modular implant assembly 1. Here, the wedge angle described above may be shown more easily, as the upper endplate 10 and lower endplate 30 and medial component 20 are configured to impart a specific, desired angle of lordosis. This angle may be adjustable as desired by the surgeon to suit the specific angle of correction or other alignment parameters required for the surgery. The medial component 20 may comprise an attachment point 28 for securing the implant assembly to an instrument or tool. The attachment point may include a keyed portion 29 for facilitating alignment of the distal end of tool with the attachment point 28, or to ensure proper orientation of the implant assembly relative to the tool once the two are coupled together.

Figure 6:
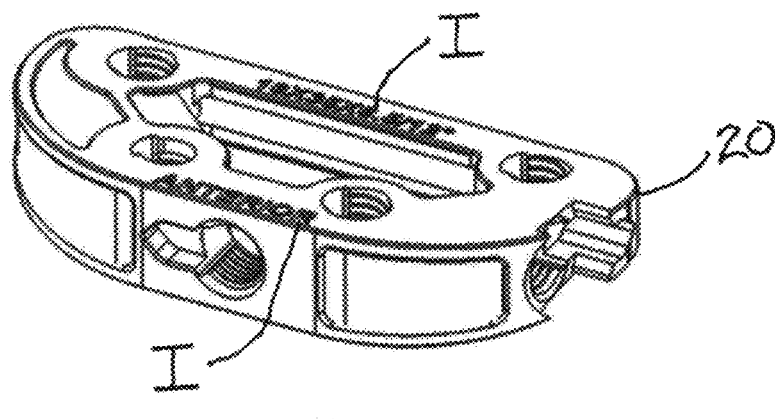
FIG. 6 is a perspective view of a patient-matched, modular implant component.

FIG. 6 depicts one embodiment of a medial or central component 20 of the patient-matched, modular implant assembly. This medial component 20 may be standard, or be offered in standard dimensions and/or angles. The medial component 20 may also include indicia I in one or more locations to assist a user in identifying the standard component size desired, or to indicate the proper orientation of the medial component 20 relative to the patient's anatomy.

FIGS. 7A-C are various views of a patient-matched, modular implant 2 according to another embodiment. As depicted, the assembly may have greater height, and in certain embodiments may completely replace one or more vertebral bodies. In this regard, the implant assembly may serve as a vertebral replacement system, where the upper endplate 10 and lower endplate 30 are sized to replace an intermediate vertebral body and be matched to the vertebral bodies one level above and one level below the intermediate vertebral body.

Figure 8A:
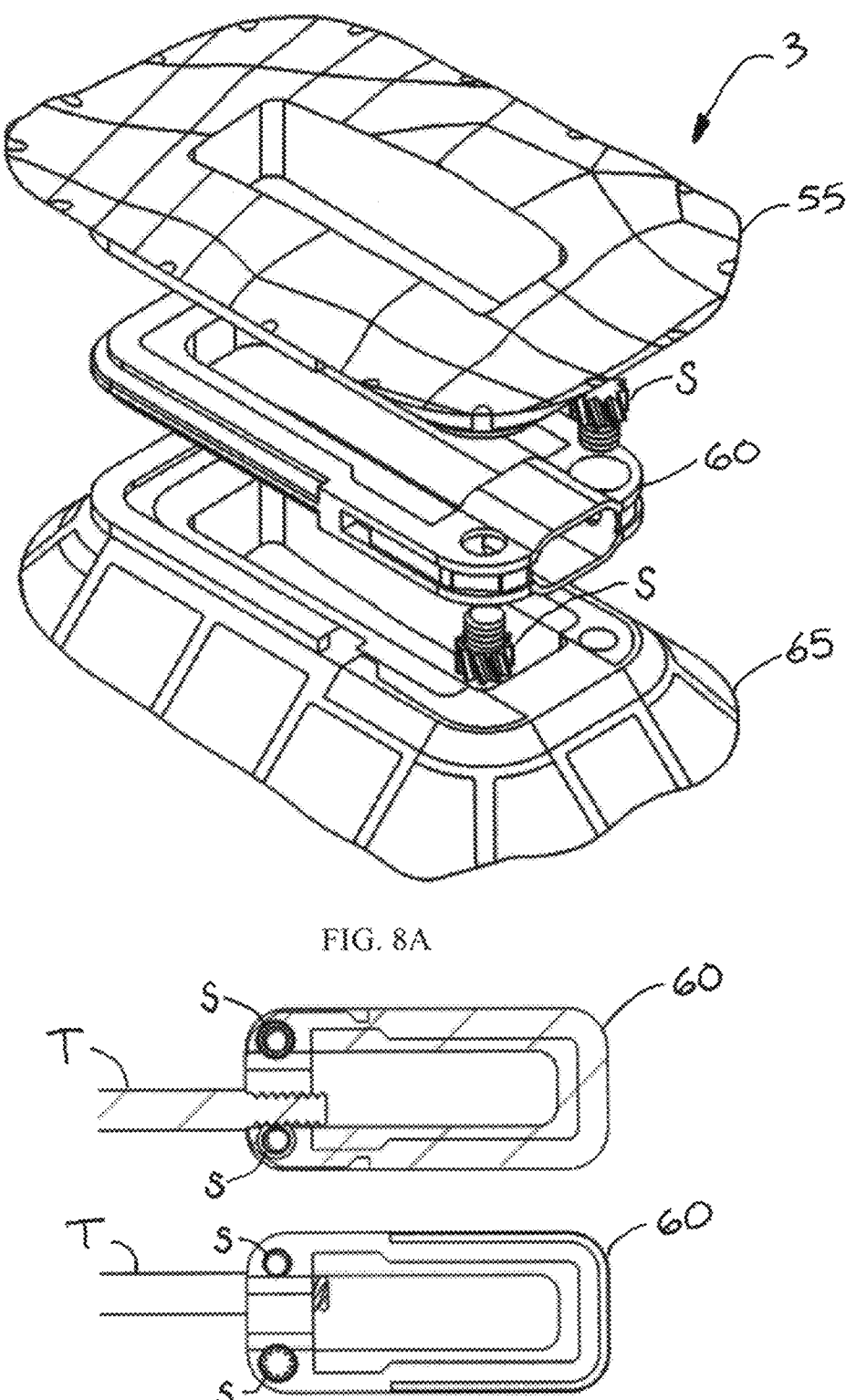

FIGS. 8A-C are various views of another patient-matched, modular implant 3 according to one embodiment. In this embodiment, the medial component 60 incorporates one or more worm screws S, which may be accessible between the upper endplate 55 and lower endplate 65 by tool T. The tool T may comprise threading to engage one or more worm screw(s) S, thereby allowing assembly of the patient-matched implant in situ. Detailed views of the tool T in relation to worm screw S are shown in FIGS. 8B-C, including in section and plan views.

The apparatus of FIG. 8A-C may be self-distracting, or may be used with a distraction instrument or assembly. For example, the upper and lower endplates 55, 65 may be coupled to a distraction instrument. The distraction instrument and endplates 55, 65 are then introduced into the vertebral space until the endplates 55, 65 engage with the vertebral endplate contours. Distraction is then initiated until the pre-surgically planned height is achieved. The medial component 60 is then introduced until positioned between the upper and lower endplates 55, 65. Distraction forces are released and the interbody component assembly features coupled together via use of tool T, thereby creating an implant assembly in-situ.

Figure 9:
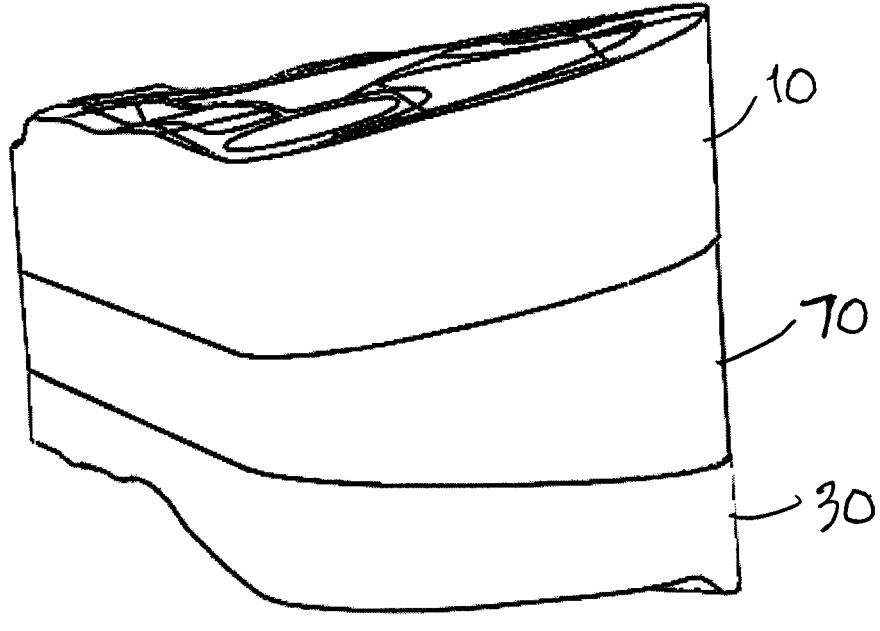
FIG. 9 is a perspective view of a modular implant according to embodiments of the present disclosure.

FIG. 9 is a perspective view of a modular implant according to an alternate embodiment. Here, a dynamic material 70 may be introduced with the modular implant assembly. The dynamic material 70 may, for example, provide one or more of rigidity, deformity, shear strength, tensile strength, etc. The dynamic material may be standardized across multiple surgeries or may be patient-specific.

Figure 10:
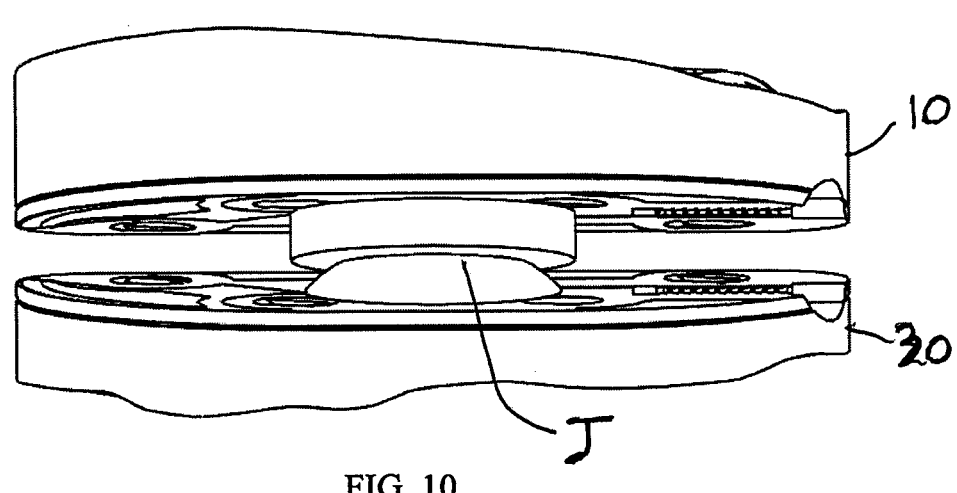
FIG. 10 is a perspective view of another modular implant according to embodiments of the present disclosure.

FIG. 10 is a perspective view of another modular implant. In this embodiment, the upper and lower endplates may comprise a mechanical joint J that permits a degree of movement between the upper and lower endplates. This may be achieved by a ball and socket joint as shown, or a pivot joint or equivalent coupling member. In this manner, the position of the upper and lower endplates 10, 30 may be dynamic and adjust after implantation.

FIGS. 11A-B are perspective views of a guide and instrument for use with the patient-matched, modular implant. Here the guide G includes a defined terminus for placement of the tool T as the modular implant assembly is inserted. The guide G may comprise a slot for inserting tool T that permits only a certain, predetermined degree of movement. The slot may be coupled to another patient-specific guide, such as a pedicle screw guide, which in turn may be used for inserting pedicle screws during the surgical procedure. FIG. 12 is a perspective view of the guide shown in FIG. 11A.

Figure 13A:
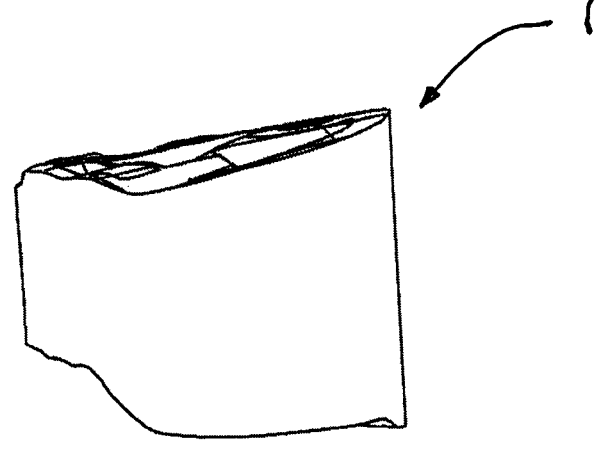
FIGS. 13A-B are various views of a patient-matched, monolithic implant according to embodiments of the present disclosure.
Figure 13B:
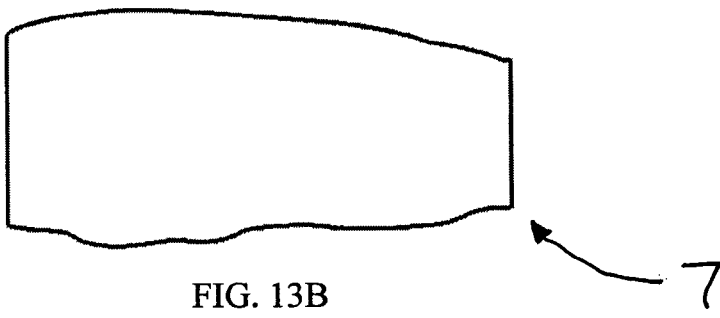

FIGS. 13A-13B depict a monolithic patient-matched implant 7 according to embodiments of the present disclosure. The primary difference over the previously described embodiments is that, as opposed to multiple components, these implants 7 comprises a single, integrated body.

Figure 14A:
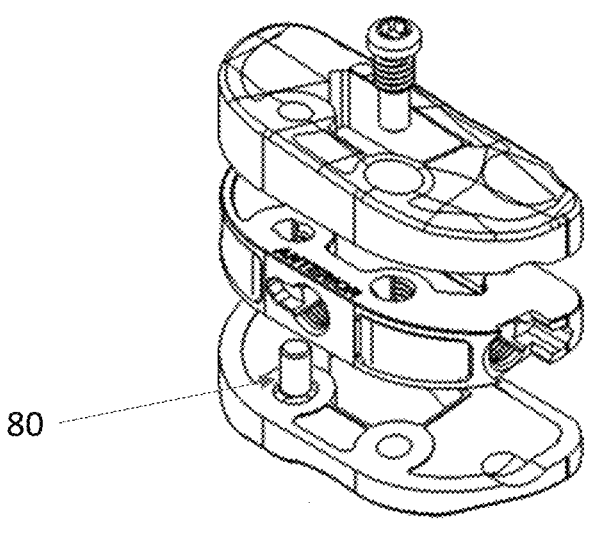
FIGS. 14A-B show perspective views of a patient-matched, modular implant assembly according to an alternate embodiment of the present disclosure.
Figure 14B:
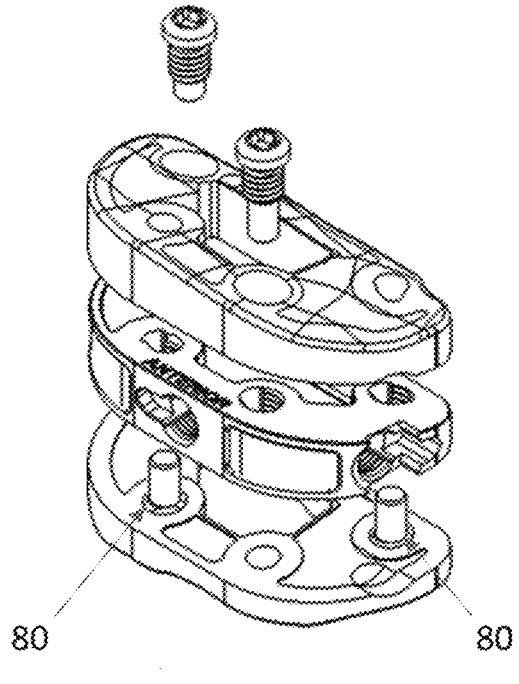

FIGS. 14A-B depict an alternative embodiment of the modular implant comprising one or more pins 80 utilized to secure the upper endplate, lower endplate and medial component together, which may occur during or prior to the surgical procedure. Pins 80 may be fitted through the modular implant 1 using, for example, a press fit, an interference fit or frictional fit.

Methods of use are also described herein. According to one embodiment, patient anatomical data is acquired by a user, preferably in the form of images (such as a CT scan). The patient data is then segmented and converted into a 3D model representing the patient's anatomy. Based on input from the surgeon, the 3D model of the patient's anatomy is adjusted. During this step, the region of interest to be treated is examined and the maximum length, width, height and wedge angle(s) are determined. In embodiments, these dimensions are determined through an analysis of the virtual vertebral endplates utilizing an augmented reality system.

Based on the determination of maximum length, width, height and wedge angle, the maximum footprint of a device that is able to conform to the patient anatomical data is determined (preferably including the Length and Width). Once the length and width are determined, an algorithm may be used to determine the height and wedge angle of the device. Next, the optimal medial component dimensions are determined (Length, Width, Height, Wedge Angle). Once the standard medial component dimensions are determined, the upper and lower endplates are designed such that the entire assembly may be configured as one conglomerate implant. In designing the upper and lower endplate geometries, the upper surface of the upper endplate is defined by the lower surface of the upper vertebral body, and the lower surface of the upper endplate is defined by the upper surface of the medial component. The same steps are applied to the lower endplate and design of the opposite surfaces of the patient's vertebral endplates and lower surface of the medial component.

In embodiments, the methods described herein involve robotic, computer-aided or other programmable equipment, or involving virtual or augmented reality systems. For purposes of streamlining the present disclosure, such equipment and systems are described in U.S. Pat. No. 11,633,254, which is incorporated by reference herein in its entirety.

The patient specific surfaces may include any number of protrusions, depressions, and contours to substantially conform to the patient's anatomy. For example, the patient specific surfaces may comprise multiple portions that are adapted to contact two different planes formed by two distinct portions of the patient's anatomy. The patient specific surfaces are adapted to one or more of: align the insert in a predetermined position with respect to the patient's anatomy; hook around a portion of the patient's anatomy; prevent unintended or inadvertent movement of the insert during a surgical procedure; and displace soft tissue. In one embodiment, the patient specific surfaces comprise relatively thin extensions to displace soft tissue. By protruding at least partially around and substantially conforming to different portions of the patient's anatomy, the patient specific surfaces generally "hook" at least partially around (or to) the patient's anatomy. Thus, the surfaces may contact at least two different planes formed by distinct surfaces of the patient's anatomy. Accordingly, the insert is adapted to at least partially fit and substantially conform to predetermined portions of one or more vertebrae during the surgical procedure.

The patient specific surfaces help position the implant and keep it in position in a predetermined position and orientation. Furthermore, the combination of patient specific surfaces formed on various locations of the implant may decrease the possibility of improper placement of the interbody guide in relation to the patient's anatomy. The surgeon may also receive tactile feedback when advancing the insert between two adjacent vertebrae, such as a clip, snap, or vibration when the insert is properly aligned with, and received between, the vertebrae.

The projections may also be adapted to bias into a predetermined orientation with respect to the patient's anatomy. Accordingly, the material of the insert may be selected to allow a surgeon bend or stretch to hook around the patient's anatomy. In one embodiment, the insert or portions thereof, may be manufactured from a material that is at least partially flexible or deformable. In another embodiment, the insert is manufactured from a material with shape memory, such as Nitinol. In this manner, when properly aligned with the patient's anatomy as planned, the insert may be releasably retained in a predetermined alignment with respect to the patient's anatomy.

Additionally, or alternatively, the projections may be asymmetrical. Thus, in one embodiment, one projection has a shape and/or size that is different than the other projection. For example, one projection may have a different thickness, contour, or length than the other projection. The asymmetric shape or size of the projections may be planned to provide a predetermined correction to the patient's spine. Similarly, the asymmetric projections may be shaped for use with a defect of the patient's spine. Additionally, the angle and orientation of each projection with respect to the distal surface of the insert can be varied to match the anatomy of the patient, or to avoid a portion of the patient's anatomy. In one embodiment, the shape of the projections does not provide correction of deformities of the patient's anatomy. In another embodiment, the shape of the projections provides at least some correction of the patient's deformity. Portions of the projections may have a tapered shape that can be used to distract the vertebrae. For example, the distal portion of each projection may comprise a full-radius or bullet-shaped nose for ease of insertion. Additionally, or alternatively, the distal portions may have a wedge shape.

Other benefits achieved from the use of these patient-specific or patient-matched apparatus of all embodiments of the present disclosure include: providing means to achieve quick and controlled removal of bone; providing spatial orientation of cutting tools used during the procedure; ensuring correct orientation of cuts, both through controlled guiding of the instrument and visualization during the pre-surgical planning process; providing accurate calculation of deformity correction, prior to cutting; providing accurate bone resection, which in turn ensures deformity correction; depth controlled cutting restrictions to protect neural and vascular elements; controlled cutting vector and avoiding contact or injury to neural elements; and ability to provide approach for cuts in a posterior, anterior, oblique, posterior lateral, transforaminal or direct lateral approach.

One having skill in the art will appreciate that embodiments of the present disclosure may have various sizes. The sizes of the various elements of embodiments of the present disclosure may be sized based on various factors including, for example, the anatomy of the patient, the person or other device operating with or otherwise using the apparatus, the surgical site location, physical features of the devices and instruments used with the devices described herein, including, for example, width, length and thickness, and the size of the surgical apparatus.

Embodiments of the present disclosure present several advantages over the prior art including, for example, the speed and efficacy of the procedure, the minimally invasive aspects of the procedure, the disposability of the prototype devices, the ability to introduce customized implements or tools to the surgical site with minimal risk and damage to the surrounding tissue, lower risk of infection, more optimally placed and/or oriented guides and implantable devices, a more stable and controlled method of placing and inserting of apparatus associated with the surgical procedure further reducing the likelihood of the apparatus becoming misaligned or dislodged, and fewer and/or less expensive tools and instruments in a surgical site, among other advantages. For example, the embodiments reduce the number and need for multiple trays, instruments and different size devices used in a particular surgery, thereby reducing the cost of the equipment necessary to complete the surgery. The embodiments also reduce the cumulative radiation exposure to both the surgeon and medical professionals in the operating environment and the patient.

Additionally, the use of patient-matched apparatus as described herein are well-suited to facilitate quicker bone removal and instrumentation of the patient's boney anatomy and/or decrease surgical time and associated risk to the patient. These novel apparatus also increase the accuracy of surgical procedures by providing patient matched surfaces to conform to a predetermined alignment or positioning with respect to the patient's anatomy. In this manner, the use of patient-matched apparatus described herein decrease the amount of fluoroscopy required to verify or correct the alignment of the guide, decreasing radian expose to medical staff as well as the patient.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, polyethylene, photo-polymers, resins, particularly fiber-encased resinous materials rubber, latex, synthetic rubber, synthetic materials, polymers, and natural materials.

With respect to the embodiments described above, it is expressly understood that such embodiments may be incorporated for use in practicing the novel methods described herein. In certain embodiments, those methods may comprise greater or fewer steps than as described above. By way of example, but not limitation, one step for use with the various embodiments described above may comprise the use of various technologies for capturing a patient's unique morphology, and subsequently mapping and/or planning the fabrication of a device comprising one or more "patient matched" surfaces or features for complementing that unique morphology. Further, such devices may be further optimized with respect to the unique data associated with the patient, such that the device may be matched with specific devices for use during the surgical procedure, or oriented around the patient's own anatomy to achieve, for example, one or more desired insertional trajectories (which may be verified in a pre-operative setting). Variations on this step, and the inclusion or exclusion of additional steps described herein are expressly contemplated by the present disclosure.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the information and materials supplied with the provisional patent applications from which this application claims priority are expressly made a part of this disclosure and incorporated by reference herein in their entirety.

Additionally, although the intervertebral implants or cages described throughout this disclosure are particularly well-suited for implantation into the spinal column between two target vertebrae, and although much of the discussion of the present disclosure is directed toward their use in spinal applications, advantages offered by embodiments of the present disclosure may also be realized by implantation at other locations within a patient where the positioning or "fusion" of two or more bony structures may be desired. As one of skill in the art will appreciate, the present disclosure has applications in the general field of skeletal repair and treatment, with particular application to the treatment of spinal injuries and diseases. It should be appreciated, however that the principles of the present disclosure can also find application in other areas.

It is expressly understood that where the term "patient" has been used to describe the various embodiments of the disclosure, the term should not be construed as limiting in any way. For instance, a patient could be either a human patient or an animal patient, and the apparatus and methods described herein apply equally to veterinary science as they would to surgical procedures performed on human anatomy. The apparatus and methods described herein therefore have application beyond surgical procedures used by spinal surgeons, and the concepts may be applied to other types of "patients" and procedures without departing from the spirit of the present disclosure.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and\or reducing cost of implementation.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A modular, patient-matched implant assembly, comprising:
 an upper endplate;
 a lower endplate;
 a medial component selectively positionable between the upper endplate and the lower endplate and comprising at least a top surface and a bottom surface;

the upper endplate comprising a first surface and a second surface, the first surface comprising one or more patient-specific contours determined from the anatomical data of a specific patient, the second surface complementary to the top surface of the medial component;

the lower endplate comprising a first surface and a second surface, the first surface comprising one or more patient-specific contours determined from the anatomical data of a specific patient, the second surface complementary to the bottom surface of the medial component;

wherein the upper endplate, lower endplate and medial component are secured together by one or more screws; and wherein the assembly comprises two sets of screws secured perpendicular to the medial component, a first set of the two sets of screws oriented in a first direction and a second set of the two sets of screws oriented in a second direction.

2. The modular, patient-matched implant assembly of claim 1, wherein the patient-matched implant assembly is configured for a TLIF trajectory, an ALIF trajectory, a DLIF trajectory, a PLIF trajectory, a TLIFO trajectory, an OLIF trajectory, a XLIF trajectory, or a cervical interbody trajectory.

3. The modular, patient-matched implant assembly of claim 2, wherein the leading edge of the implant assembly comprises a tapered shape to facilitate insertion along a chosen trajectory.

4. The modular, patient-matched assembly of claim 1, wherein the first direction is an opposing direction to the second direction.

5. The modular, patient-matched implant assembly of claim 1, wherein the medial component is provided in a variety of lengths, widths, heights and angles.

6. The modular, patient-specific implant assembly of claim 5, wherein the lengths, widths, heights and angles of the medial component are standardized.

7. The modular, patient-matched implant assembly of claim 1, wherein at least one of the upper endplate, lower endplate and medial component comprise a plurality of apertures.

8. The modular, patient-matched implant assembly of claim 7, wherein one or more of the plurality of apertures comprise a porous structure.

9. The modular, patient-matched implant assembly of claim 8, wherein the porous structure is patient-specific and determined from the anatomical data of the specific patient.

10. The modular, patient-matched implant assembly of claim 1 further comprising a central aperture that spans the upper endplate, lower endplate and medial component.

11. The modular, patient-matched implant assembly of claim 1, wherein the one or more patient-specific contours of the upper and lower endplates are additively manufactured.

12. The modular, patient-matched implant assembly of claim 1, wherein the at least a top surface and a bottom surface of the medial component comprise a slot for mating with adjoining surfaces of the upper and lower endplates.

13. The modular, patient-matched implant assembly of claim 1, further comprising a tool having a threaded portion, the threaded portion configured to engage the one or more screws for securing the upper and lower endplates to the medial component.

14. The modular, patient-matched implant assembly of claim 1 further comprising at least one pin.

15. The modular, patient-matched implant assembly of claim 14, wherein the at least one pin is secured to the medial component by a friction fit.

16. The modular, patient-matched implant assembly of claim 1, wherein the at least one pin further comprises a friction fit with the upper endplate.

17. The modular, patient-matched implant assembly of claim 1, wherein the at least one pin further comprises a friction fit with the lower endplate.

18. The modular, patient-matched implant assembly of claim 1, wherein the implant assembly is assembled in situ.

19. A method for fabricating a modular, patient-matched implant comprising the steps of:

acquiring patient anatomical data, preferably in the form of images;

segmenting and converting the data into a 3D model representative of the patient anatomical data;

adjusting the 3D model based upon input from at least one individual;

determining a maximum length, width, height and wedge angle(s) for the specific patient;

determining a maximum footprint of a device that is able to conform to the patient anatomical data;

determining the height and wedge angle of the device for manufacture specific to the patient;

determining a first dimension of a medial component of the device;

determining a second and third dimensions of an upper and lower endplates, including:

(a) defining contours of an upper surface of the upper endplate to match a lower surface of the adjacent vertebral body;

(b) defining contours of a lower surface of the upper endplate to match an upper surface of the medial component;

(c) defining the contours of a lower surface of the lower endplate to match an upper surface of the adjacent vertebral body; and (d) defining the contours of an upper surface of the lower endplate to match a lower surface of the medial component;

wherein the patient-matched implant further comprises a first set of two sets of screws oriented in a first direction and a second set of two sets of screws oriented in a second direction, the first and second set of screws inserted through the medial component, the upper endplate and the lower endplate.

\* \* \* \* \*